United States Patent [19]

Brown

[11] Patent Number: 5,985,559
[45] Date of Patent: Nov. 16, 1999

[54] SYSTEM AND METHOD FOR PREVENTING, DIAGNOSING, AND TREATING GENETIC AND PATHOGEN-CAUSED DISEASE

[75] Inventor: Stephen J. Brown, Mountain View, Calif.

[73] Assignee: Health Hero Network, Mountain View, Calif.

[21] Appl. No.: 08/850,840

[22] Filed: May 3, 1997

Related U.S. Application Data

[63] Continuation-in-part of application No. 08/847,009, Apr. 30, 1997.

[51] Int. Cl.⁶ .............................. C12Q 1/68; C12M 1/34; C12M 3/00; G01N 33/48
[52] U.S. Cl. ...................... 435/6; 435/285.1; 435/287.1; 435/287.2; 435/288.7; 436/63
[58] Field of Search ........................ 435/6, 172.1, 172.3, 435/4, 283.1, 285.1, 287.1, 288.7, 287.2; 436/63

[56] References Cited

U.S. PATENT DOCUMENTS

| | | | |
|---|---|---|---|
| 5,307,263 | 4/1994 | Brown | 364/413.09 |
| 5,714,319 | 2/1998 | Joutel et al. | 435/6 |

OTHER PUBLICATIONS

Skolnick et al. Simultaneous Analysis of Multiple Polymorphic Loci Using Amplified Sequence Polymorphisms (ASPs). Genomics. 2: 273–279.

*Primary Examiner*—Nancy Degen
*Attorney, Agent, or Firm*—Lumen Intellectual Property Services

[57] ABSTRACT

Genetic testing allows an individual to determine whether or not he or she has a predisposition to a certain disease. The degree of expressivity of a certain disease will be determined in part by an individual's environment and lifestyle. The present invention interprets a patient's gene sequence and his or her environment and lifestyle to come up with a personalized prognosis. This procedure can be repeated many times over the course of a disease state to monitor a patient's condition. In addition, disease-causing pathogens can also have their genes sequenced. Using these sequences in combination with information about a patient's environment and lifestyle, it is possible to come up with a personalized treatment plan, ideally to eliminate the pathogen. It is also possible to use the procedure described above to monitor the course of the disease-state produced by a pathogen. Finally, a genotype-to-phenotype map or database can be constructed for developing better treatments and for research purposes.

8 Claims, 6 Drawing Sheets

SYSTEM AND METHOD FOR PREVENTING, DIAGNOSING, AND TREATING GENETIC AND PATHOGEN-CAUSED DISEASE

RELATED U.S. APPLICATION DATA

This application is a continuation-in-part of co-pending application Ser. No. 08/847,009, filed Apr. $30^{th}$, 1997.

FIELD OF THE INVENTION

This invention relates generally to a system for the prevention, diagnosis, and treatment of genetic and pathogen-caused disease. In particular, it relates to a system that makes use of a health monitor for providing a personalized prognosis based on an individual's gene sequence, environment and lifestyle.

BACKGROUND OF THE INVENTION

Most major chronic conditions are related to patient environment and lifestyle factors that act on preexisting genetic dispositions to diseases. This is true of many cancers, hypertension, heart disease, diabetes, and mental illnesses. Ways to prevent or reduce the severity of such diseases include changing a patient's environment and/or lifestyle (e.g. diet, exercise, stress, substance abuse, pollution) or by following therapeutic regimes that lessen the impact of environment or lifestyle (e.g. taking cholesterol lowering drugs).

One of the difficulties in changing patient behavior is that a prognosis based on lifestyle factors is very imprecise and it is easy for a patient to rationalize why such a prognosis does not apply to him or her, or at least not yet. Everyone knows an example of someone who smoked and drank and lived to a ripe old age. Everyone also knows of someone who was health-conscious and jogged every day, yet died of a heart attack. Because a prognosis is vague and difficult to individualize to a patient, many patients do not change their behavior until it is too late.

A major advance in preventative medicine is the ability to test for a genetic predisposition for certain diseases. Unfortunately, the human genome is incredibly complex and based on a gene sequence alone, there are still too many degrees of freedom to make an accurate and personalized prognosis for an individual patient. This is especially true for genetic diseases that are heavily influenced by environmental and lifestyle factors.

In order to use genotypes for disease prevention, it is necessary to. develop better methods for profiling a patient's phenotype in order to reduce the degrees of freedom and provide a more accurate prognosis. It may also be necessary to continue to profile the patient over time in order to monitor behavior and adjust the prognosis. In addition, it is hoped a patient will be more motivated to adhere to a prescribed treatment or regimen if he or she can easily see the effects of changes in behavior.

Diseases that are not caused by genetic factors are often caused by pathogens. Many virus-induced diseases such as hepatitis, AIDS, and herpes are incurable in part because of the high mutation rate of the pathogens. Vaccines created to combat such pathogens are quickly rendered ineffective.

With the recent advances in biotechnology, it is now possible to sequence genes to create a genetic profile of an organism. Thus it is possible to determine the specific genetic makeup of a pathogen in a patient, and to use that information to create a patient-specific treatment or vaccine. Unfortunately, because genomes are so complex and because the patient phenotype upon which the pathogen acts is so variable, there are too many degrees of freedom to tailor a precise treatment to a patient's need. In order to use pathogen genotypes in treatment of disease, it is necessary to develop better methods of profiling a patient's phenotype in order to reduce the degrees of freedom and provide a more accurate prognosis. It may also be necessary to monitor the patient over time in order to determine the effectiveness of the treatment and to adjust the treatment to the patient's response.

All of these approaches are very cost-intensive since they are predicated on collecting patient-specific genotype and phenotype data. Using traditional data collection methods, in view of the rapidly growing genotype knowledge, is therefore inadequate.

OBJECTS AND ADVANTAGES OF THE INVENTION

Accordingly, it is the primary object of the present invention to determine the expressivity of a condition associated with a particular genotype. It is another object of this invention to provide a patient with a personalized prognosis based on his or her gene sequence, environment, and lifestyle. It is yet another object of this invention to allow monitoring of a patient's condition over time in order to track the effectiveness of treatments and changes in patient behavior.

Another object of the invention is to allow treatment of a pathogen-caused disease. Another object of this invention to provide a patient with a personalized prognosis based on a pathogen's gene sequence and the patient's environment and lifestyle. A further object of this invention is to allow monitoring of a patient's condition over time in order to track the effectiveness of treatments and mutation rate of the pathogen.

SUMMARY OF THE INVENTION

These objects and advantages are attained by the system and method of the present invention. The system consists of a health monitor, such as the Health Buddy shown in FIG. 3, which can read a patient's gene sequence, as derived from a gene sequencing apparatus, as shown in FIG. 1. The health monitor is preferably connected via a network to a database, as shown in FIG. 2 which has resources, e.g., databases, containing known gene sequences and generic or associated scripts. The health monitor interprets the genetic data from the gene sequencing apparatus and retrieves the appropriate associated script from the database. These scripts contain information relevant to the disease associated with the gene sequence. They also contain questions about a patient's environment or lifestyle which the patient or clinician answers and sends back over the network to the database. Another, secondary script based on the patient's answer may then be generated and sent back to the patient. Thus the secondary scripts are wholly dynamic, meaning they are unique documents generated specifically as a result of the patient-specific answers. The end result is a determination of expressivity of the condition, or phenotype, associated with the patient's genotype, or gene sequence. These events can be repeated over the course of a disease state, allowing the patient's condition to be monitored. In addition, effectiveness of treatments is determined and changes in patient behavior are noted.

Another system of the invention involves a treatment for pathogen-caused diseases. This system also consists of a health monitor, such as a Health Buddy, which interprets a pathogen's gene sequence, as derived from a gene sequencing apparatus. The health monitor can also be used to determine a patient's phenotype. Both types of information are then used to develop a personalized treatment for the patient. The patient's condition and response to treatment can be evaluated over time by use of the health monitor. In addition, because pathogens often have a high mutation rate, their gene sequences may change. The genomes of the pathogens may be re-sequenced for such changes and, in conjunction with the patient phenotype as determined by the health monitor, a new treatment may be devised.

DETAILED DESCRIPTION

The main component of a system for determining an expressivity of a phenotype associated with a genotype is a health monitor.

Figure 1:
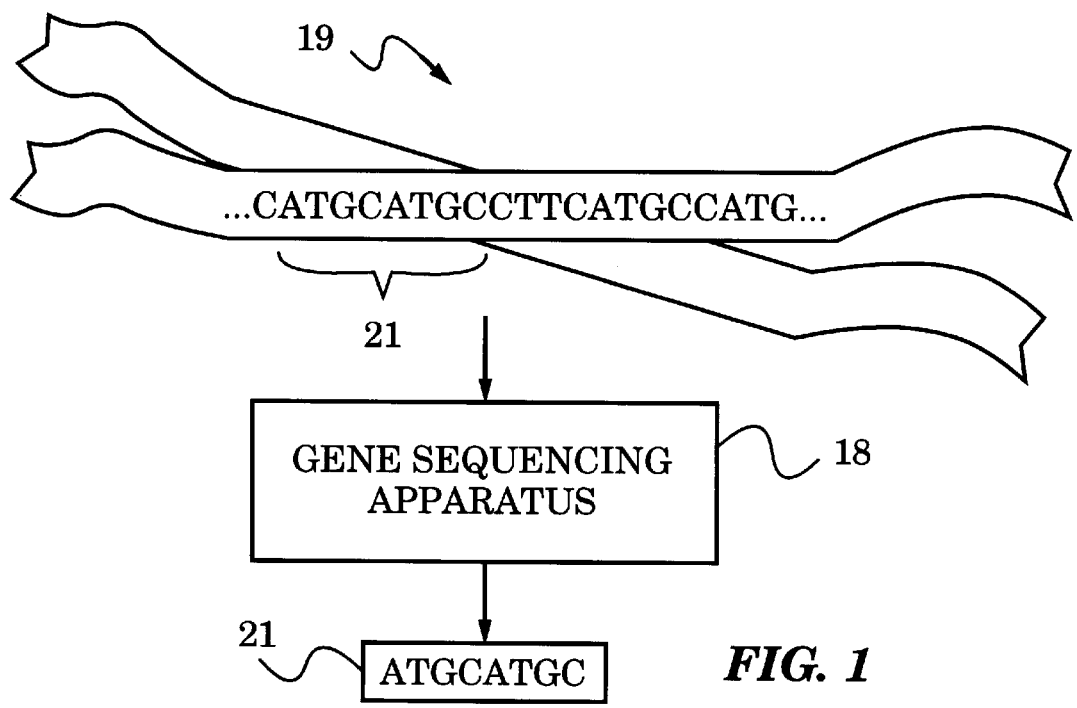
FIG. 1 is a gene sequencing apparatus.
Figure 2:
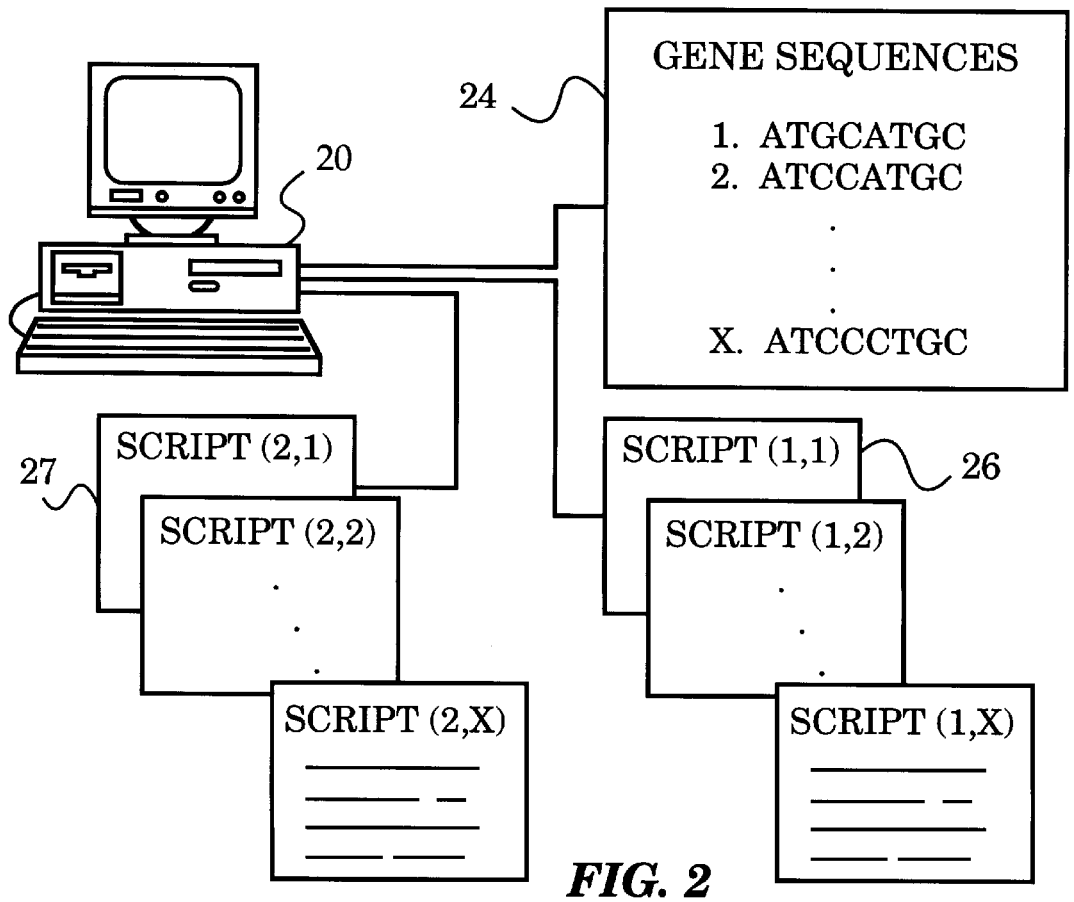
FIG. 2 is a database containing known gene sequences and associated scripts.
Figure 3:
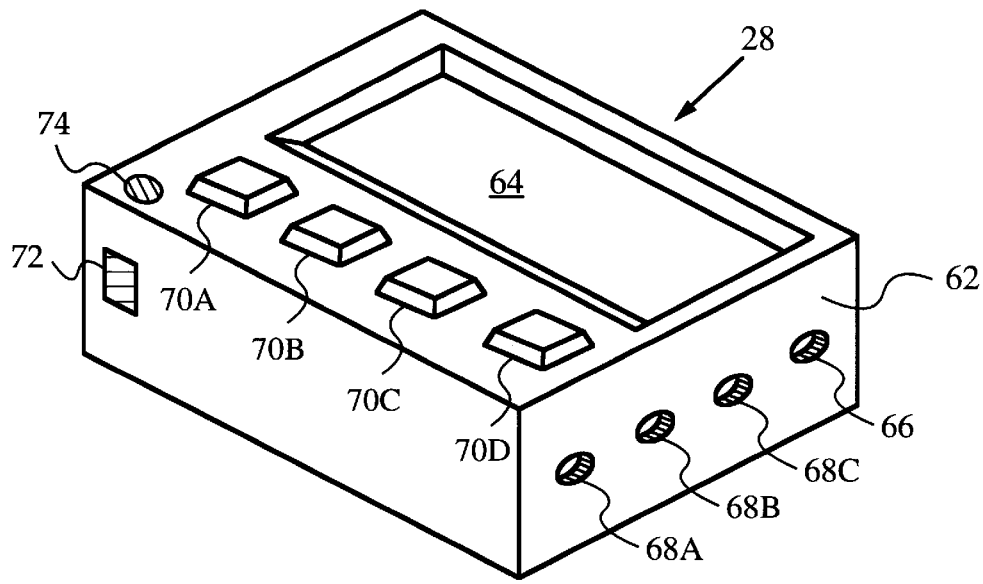
FIG. 3 is a health monitor.

In the preferred embodiment a health monitor 28 is the Health Buddy or monitoring system as illustrated in FIG. 3 and described in the inventors co-pending patent-application entitled "Monitoring System for Remotely Querying Individuals" and filed on Apr. 30, 1997. The information contained in that application is herein incorporated by reference.

Health Buddy 28 allows measurements of physiological conditions of a patient, recording of the measurements, and transmission of the measurements to a database. It consists of a hand-held, portable structure 62 with a display 64 for displaying scripts 26, 27, corresponding response choices, and prompts to the patient. In the preferred embodiment, display 64 is a liquid crystal display (LCD) for displaying four lines of text having up to twenty characters per line. Four user input buttons 70A, 70B, 70C, 70D are located on the structure. In the alternative embodiment, buttons 70A, 70B, 70C, 70D are replaced by switches or keys. Three monitoring device jacks 68A, 68B, 68C are located on the surface of structure 62 for connecting to a gene sequencing apparatus 18 and a database 20. Health Buddy 28 also includes a modem jack 66 for connection to a telephone jack through a standard connection cable (not shown).

Health Buddy 28 also includes an audio transducer, such as a speaker 72, which can notify patients when queries are unanswered. Health Buddy 28 further includes a visual indicator, such as a light-emitting diode 74, for visually notifying patients when queries are unanswered.

Figure 4:
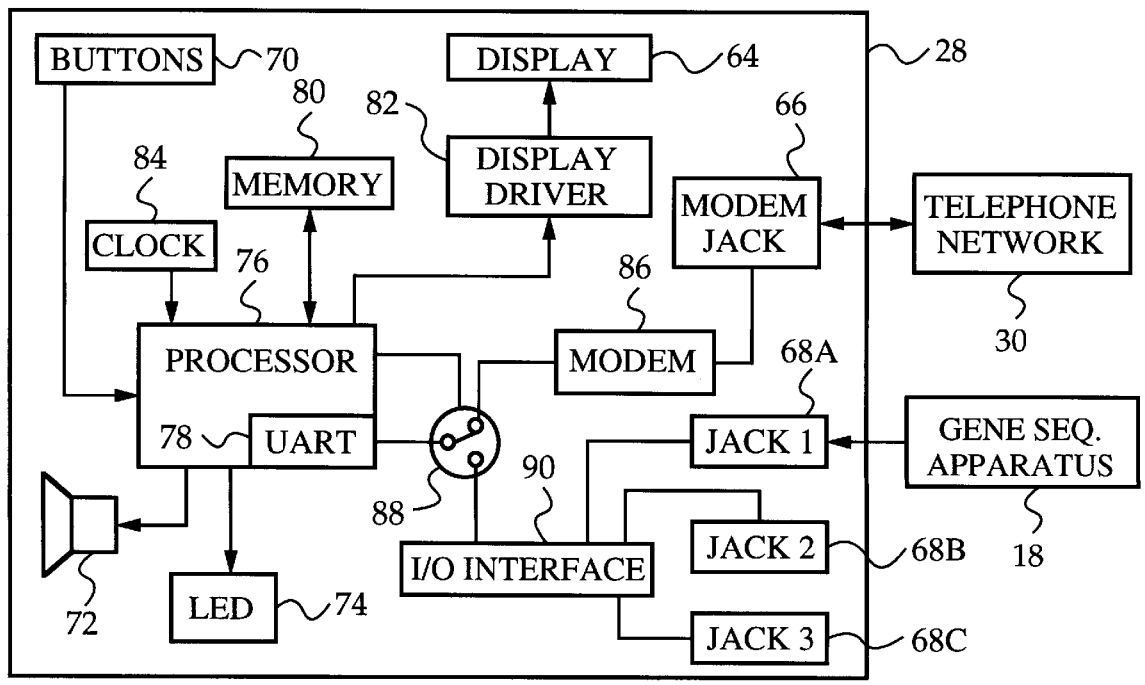
FIG. 4 is a schematic block diagram illustrating the components of the health monitor of FIG. 3.

FIG. 4 is a schematic block diagram illustrating Health Buddy 28 and its connections to telephone network 30 and gene sequencing apparatus 18 in greater detail. Health Buddy 28 consists of a microprocessor 76 and a memory 80 connected to microprocessor 76. Memory 80 stores scripts 26, 27 received from database 20 and firmware for controlling the operation of Health Buddy 28. The firmware includes a script interpreter used by microprocessor 76 to execute scripts 26, 27. Memory 80 is preferably non-volatile memory; in the preferred embodiment it is a serial EEPROM. Memory 80 also stores measurements received from gene sequencing apparatus 18, responses to queries, and the patient's unique identification code.

Memory 80 is preferably connected to microprocessor 76 using the standard two-wire $I^2C$ interface. Microprocessor 76 is preferably a PIC 16C63 processor and includes a universal asynchronous receiver transmitter (UART) 78. UART 78 is for communicating with a modem 86 and a multiple device interface 90. A CMOS switch 88 under the control of microprocessor 76 alternately connects modem 86 and interface 90 to UART 78.

Modem 86 is connected to network 30 through modem jack 66. Modem 86 is for establishing communication links between Health Buddy 28 and database 20 through network 30 and for exchanging data with database 20. The data includes scripts 26, 27 which are received from database 20, as well as responses to queries, device measurements, and the patient's identification code which modem 86 transmits to database 20. Modem 86 is preferably a complete 28.8 K modem commercially available from Cermetek Microelectronics, Inc., Sunnyvale, Calif. or any other suitable communications device.

Device interface 90 is connected to device jacks 68A, 68B, and 68C. Device interface 90 is for interfacing with a number of monitoring devices, such as gene sequencing apparatus 18 through jacks 68A, 68B, and 68C. Device interface 90 is designed to receive device measurements and output the measurements to microprocessor 76 for storage in memory 80. In fact, device interface 90 operates under the control of microprocessor 76 to collect device measurements from gene sequencing apparatus 18.

User input buttons 70, (70A–D) speaker 72, LED 74, a clock 84, and a display driver 82 are connected to microprocessor 76. Clock 84 indicates the current date and time to microprocessor 76. Display driver 82 is connected to display 64 and operates under the control of microprocessor 76 to display information on display 64.

In the preferred embodiment, health monitor 28 is connected to gene sequencing apparatus 18, which has the ability to sequence a given part or sequence of a patient's genome 19. Health monitor 28 receives a gene sequence 21 from gene sequencing apparatus 18 and then sends the information by network 30 to remote database 20, which contains known gene sequences 24 and their associated scripts 26. Database 20 is then able to match the patient's gene sequence 21 with known gene sequences 24 and identify the associated script 26 to be sent back to the health monitor 28 over the network 30. Health monitor 28 displays script 26 on a screen 22 to the patient. Script 26 may tell the patient that based on gene sequence 21, he or she has no predisposition for a disease. However, if based on gene sequence 21, it is likely the patient does have a predisposition for a disease, script 26 will contain questions about the patient's environment or lifestyle. The patient or clinician can then answer the questions on script 26 and send the response back over network 30 to database 20. Database 20 has the ability to generate another dynamic script 27, based on the patient's response. In other words, the answers to questions in script 26 are used to assess the patient's status (this may be performed by a doctor or an appropriate health-care decision-making program) and generate dynamic script 27 to gain better insight or more information about the patient.

The above steps may be repeated as necessary since any number of follow-up scripts can be generated. Using gene sequence 21 and the information provided by the patient, health monitor 28 may also be able to provide a prognosis of the disease. This prognosis can even be sent to the patient in dynamic script 27 to increase his or her compliance with the treatment program.

Of course, it is also possible to use the system of the present invention to evaluate and/or monitor a patient's condition over a long period of time. This can be appropriate when the patient has a chronic condition warranting constant supervision and/or monitoring. In this case, scripts 26, 27 stored in database 20 can be sent to the patient over network 30 after certain time intervals. Based on the patient's response, a health care provider can evaluate the course of the disease. Treatment may be modified as necessary. In addition, the patient can see the direct effects environment and lifestyle have on their disease condition and thus be motivated to comply with the treatment. The below examples provide additional details on the use of the system of invention in particular cases.

EXAMPLE 1

Cystic Fibrosis

An example of a genetic condition that can be identified and treated using the described system is cystic fibrosis. Cystic fibrosis is caused by mutations in a gene which codes for a cystic fibrosis transmembrane conductance regulator. Mutations change the conductance of chloride ions in epithelial tissues, ultimately leading to an increase in the viscosity of mucus produced. Patients with cystic fibrosis have an average life span of forty years.

Gene sequencing apparatus 18 specific for a mutant cystic fibrosis gene sequence is used to determine whether or not a patient's genome 19 contains gene sequence 21. Health monitor 28 takes this information and sends it to database 20. Database 20 compares patient's gene sequence 21 with known mutant cystic fibrosis gene sequences 24, finds a match, retrieves script 26 associated with gene sequence 21, and then sends script 26 back to health monitor 28. Health monitor 28 displays script 26 to the patient, who may respond. Health monitor 28 then uses gene sequence 21 and the patient's response to give a prognosis as to the severity of the patient's cystic fibrosis. Using the information generated by health monitor 28, a personalized treatment can be created for the patient. Likewise, using health monitor 28, the state of the patient's cystic fibrosis can be tracked.

EXAMPLE 2

Gaucher Disease

Gaucher disease is a rare inherited enzymatic deficiency most commonly found in the Askenazi Jewish population. A genetic defect in the enzyme glucocerebrosidase results in the accumulation of the lipid glucocerebroside within lysosomes of the cell. The disease is characterized by a variable degree of expressivity among individuals containing the disease-causing gene sequences. Symptoms include anemia, bone damage, enlarged liver and spleen, as well as central nervous system damage.

Figure 5:
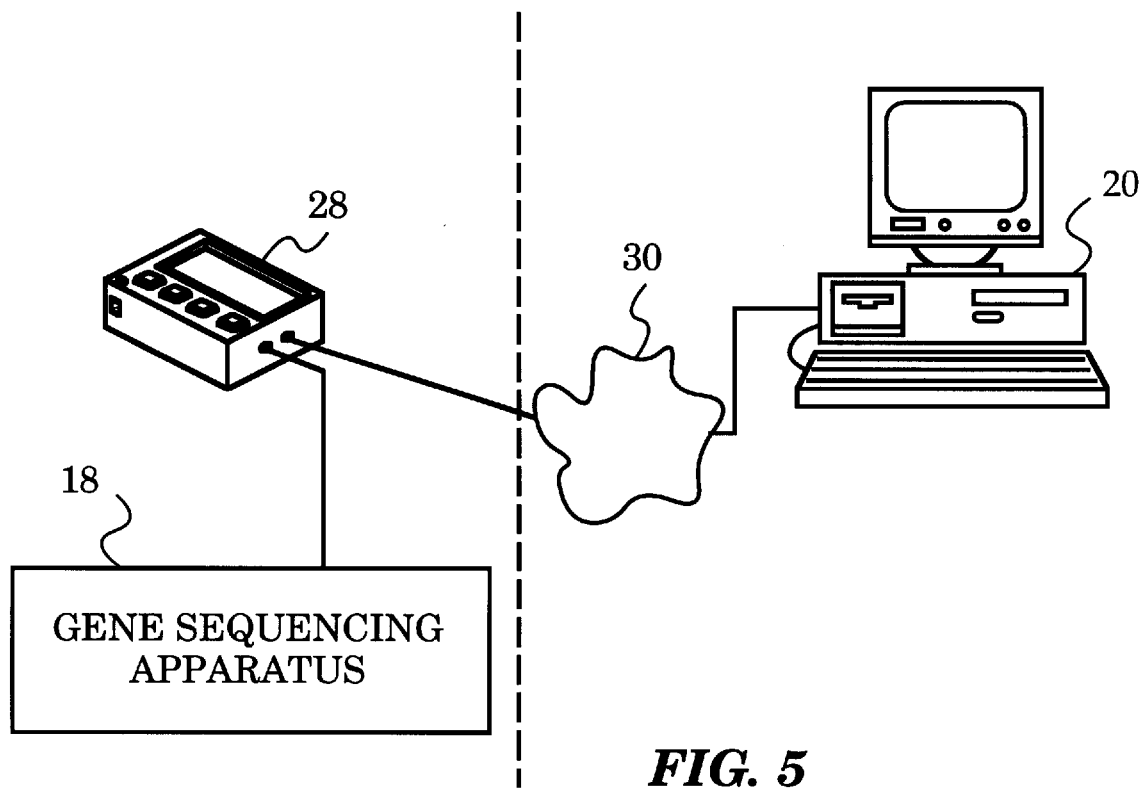
FIG. 5 is a network consisting of a gene sequencing apparatus and a database connected to a health monitor.
Figure 6:
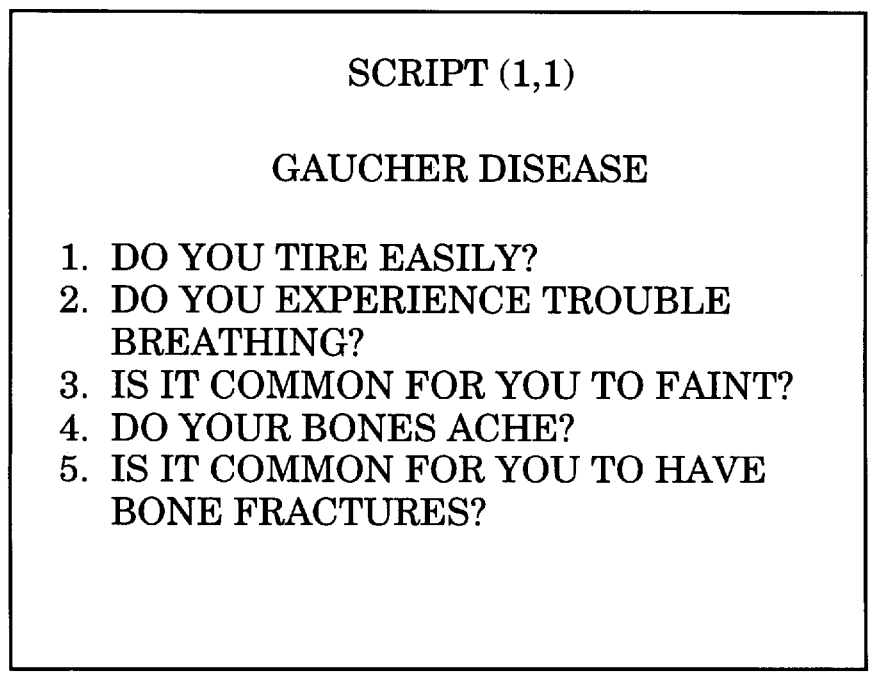
FIG. 6 is a script stored on a database.
Figure 7:
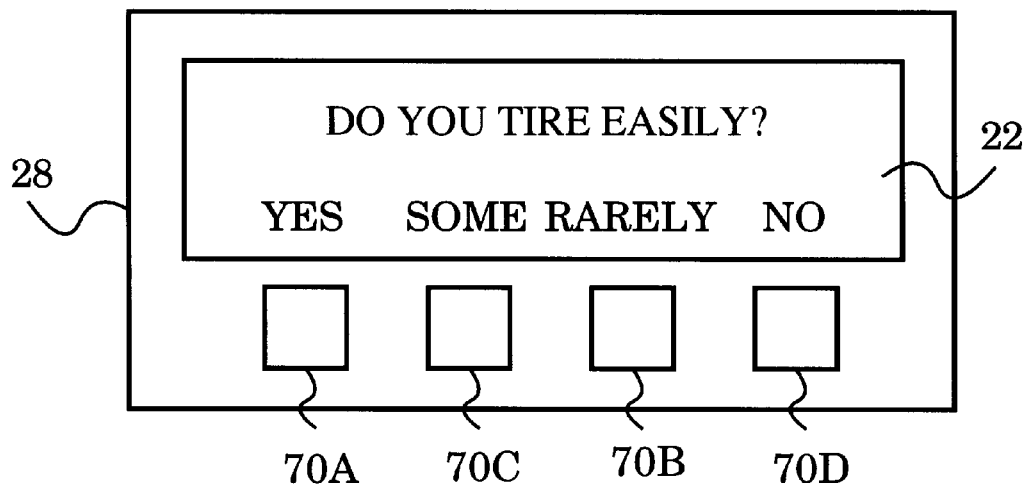
FIG. 7 is a question from a script displayed on a display of a health monitor.

As described above, the present invention can identify Gaucher disease in a patient. After identification of the disease and an initial assessment as to the state of the disease in the patient, health monitor 28 can retrieve secondary scripts 27 from database 20. Script 27, as shown in FIG. 5, contains specific questions regarding the progress of the disease in the patient. The patient or caregiver answers the questions on health monitor 28, which then sends the response back to database 20. A health care professional can then read the patient's response, and depending on the severity of the patient's condition, devise or revise treatment. Likewise, the patient's condition can be evaluated after treatment or at certain intervals using health monitor 28. Health monitor 28 can periodically retrieve scripts 27 for a patient to answer. The patient answers the questions on script 27 and then sends the response back to database 20 where a health care provider can read the response and evaluate the patient's condition.

The described system can also be used to treat a pathogen-caused disease. Health monitor 28 is connected to gene sequencing apparatus 18, which is used to sequence a pathogen present in the patient's blood. Gene sequence 21 of the pathogen is received by health monitor 28. Health monitor 28 also receives information about the patient's physical condition. Using these two pieces of information, a personalized treatment for the patient can be developed. The course of the disease in the patient can also be monitored using health monitor 28.

SYSTEM OPERATION

The above two examples explain the operation of the system of the invention from the point of view of the patient or clinician answering the questions and/or following recommendations presented in scripts 26, 27 and using gene sequencing apparatus 18. At a higher level, however, the present invention can be best understood as an entire system 100 for processing genotype and phenotype data as shown in FIG. 8A.

Figure 8A:
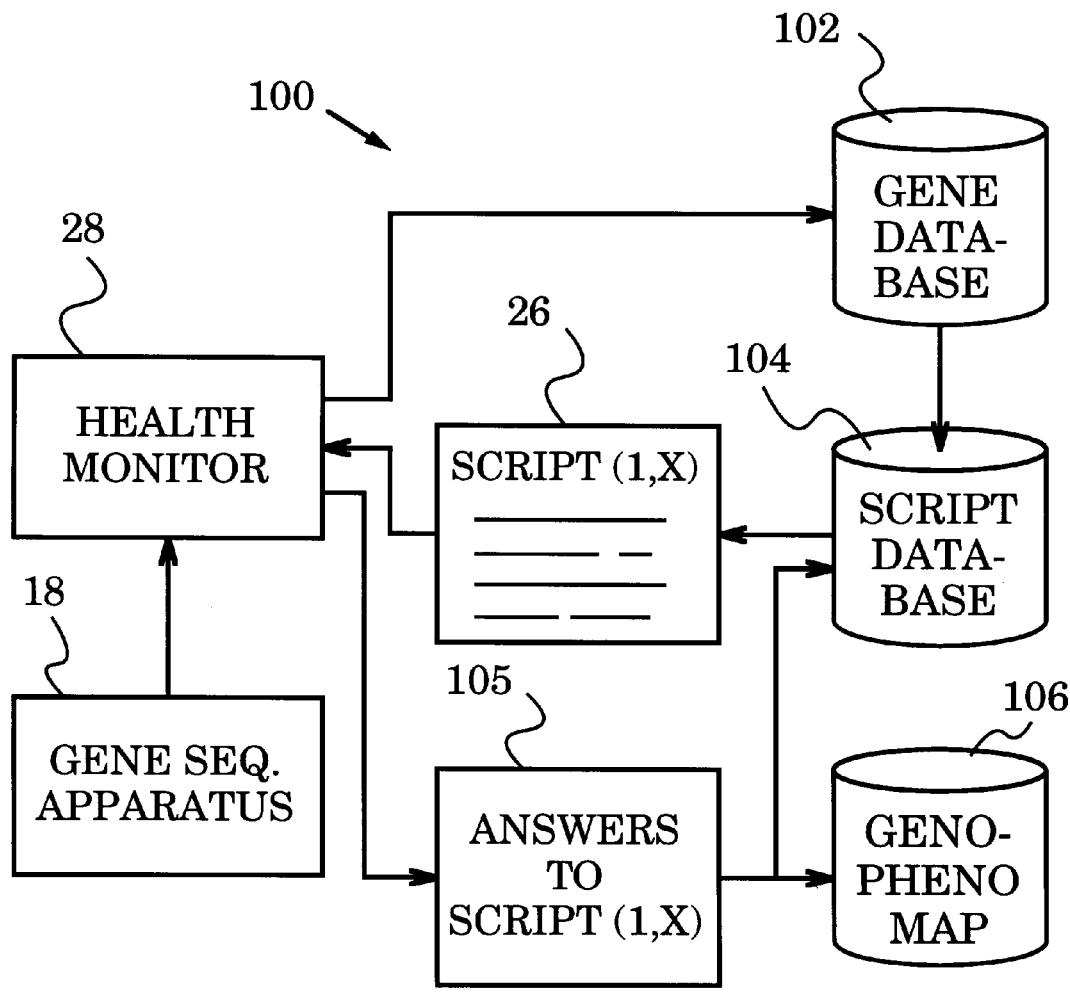
FIG. 8A is a diagram showing a first general sequence of steps in the system of the invention.

In fact, FIG. 8A illustrates the first series of steps performed by system 100. First, gene sequencing apparatus 18 sends the genotype information, i.e., gene sequence 21, to health monitor 28. Health monitor 28 forwards gene sequence 21 to a gene database 102 which contains all known gene sequences and, based on that information, identifies gene sequence 21. Then, gene database 102 contacts a script database 104 with identified gene sequence 21. Script database 104 locates associated script 26 designated (1,X) where the 1 indicates that this is the first or generic script and the X is the identifier of gene sequence 21.

Script (1,X) is sent back to health monitor 28 to be displayed and answered by the patient or the clinician assisting the patient. When ready, answers 105 to script (1,X) are relayed to a geno-pheno map 106 and back to script database 104. Geno-pheno map 106 is a consolidated database containing general and patient specific information. In fact, preferably geno-pheno map 106 is used to collect answers to all scripts.

Figure 8B:
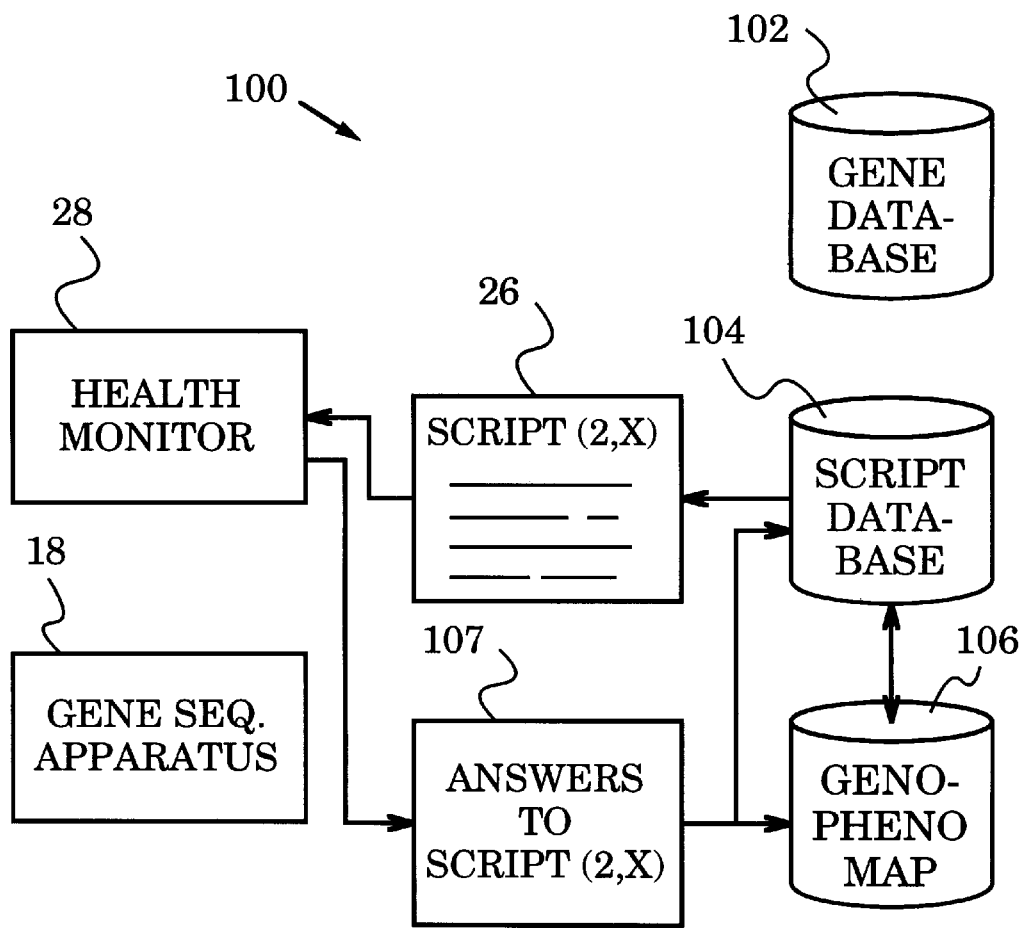
FIG. 8B is a diagram showing a second general sequence of steps in the system of the invention.

As shown in a subsequent series of steps in FIG. 8B, geno-pheno map 106 actually communicates with script database 104. In the event that a dynamic script 27 is available in script database 104 given answers 105 to script (1,X), script database 104 simply pulls up dynamic script 27 designated (2,X) where the 2 indicates that this is the second or dynamic script and the X is the identifier of gene sequence 21. Next, script (2,X) is forwarded to health monitor 28.

Once again, the patient or the clinician assisting the patient answers the questions contained in script (2,X).

Then, answers 107 to script (2,X) are returned to both geno-pheno map 106 and script database 104 as before. Clearly, an entire series of dynamic scripts (3,X), (4,X) . . . (N,X) can be sent to the patient in this iterative process.

Figure 9:
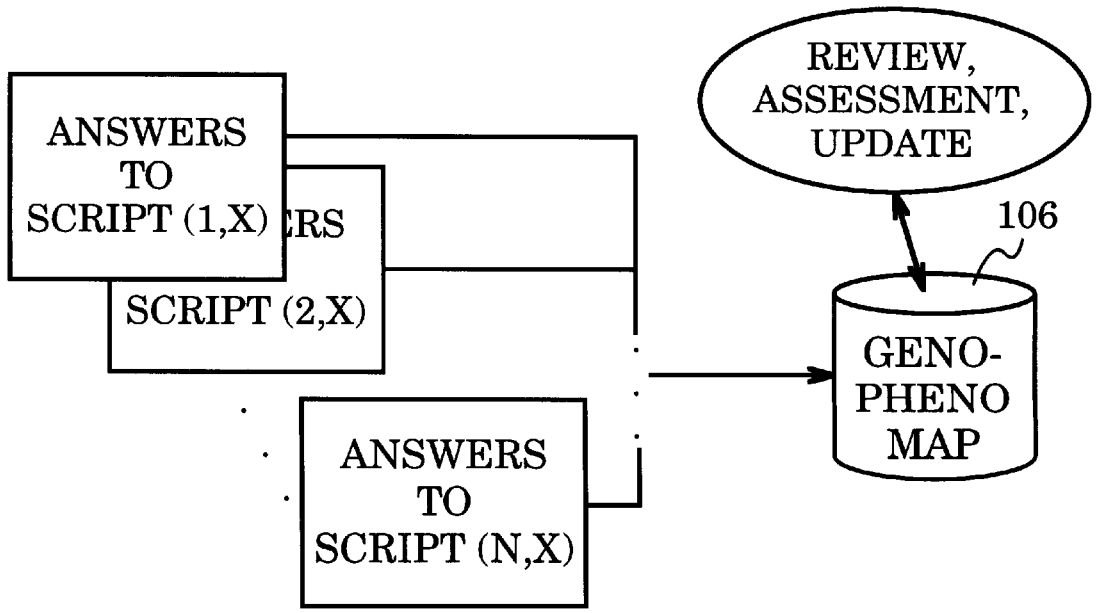
FIG. 9 is a diagram showing how the genotype and phenotype information is processed.
Figure 10:
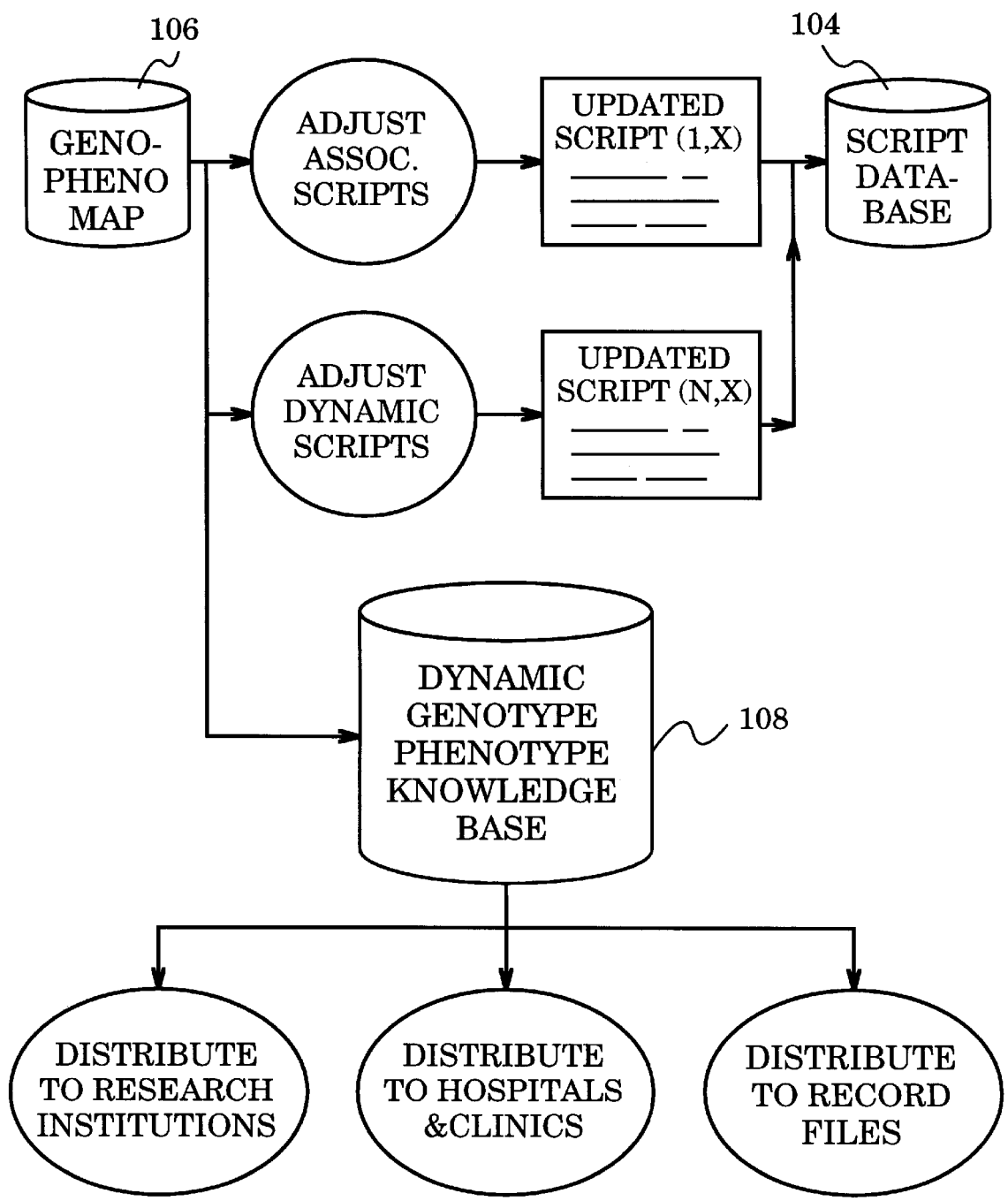
FIG. 10 is a diagram showing selected uses of a genotype-to-phenotype map (hereafter geno-pheno map).

In the event that any dynamic script 27 is not available in script database 104 or is out of date, system 100 generates an updated or new dynamic script 27, which is stored in script database 104 and relayed to health monitor 28. This situation is illustrated in FIGS. 9 and 10. During a first step, shown in FIG. 9, available answers 105, 107 . . . to scripts (1,X), (2,X) . . . (N,X) are reviewed and assessed. This process is preferably performed by an expert or a doctor. Of course, a suitable program capable of sorting and classifying the information in pheno-geno map 106 can review the answers according to well-known algorithms of artificial intelligence.

The review is followed up by an assessment to determine whether new dynamic script 27 for the particular gene sequence X is feasible or whether old dynamic script 27 should be updated. In fact, even generic script 26 can be updated or changed if the review process uncovers a general question or recommendation which should be asked or made up front. For example, this can be done if a statistical analysis of answers 107 to script (2,X) indicates a strong and previously unknown correlation of a phenotype with a genotype. Thereupon, the corresponding question or recommendation is added to script 26 during the update step.

FIG. 10 illustrates the update procedure itself. An adjustment performed on associated scripts generates updated scripts (1,X). These scripts are forwarded to script database 104 and used as described above. Analogously, an adjustment performed on dynamic scripts generates updated scripts, i.e. updated script (N,X). Of course, the word updated can also indicate the creation of a new script.

In addition to adjusting scripts, geno-pheno map 106 can be used to build up a dynamic genotype-phenotype knowledge base 108. The information in base 108 represents the current state of knowledge about genotype to phenotype mapping and as such is an extremely useful tool for any persons involved in gene research. As indicated, the up-to-date information from knowledge base 108 can be distributed to research institutions to aid in developing new treatments, monitoring programs and prognoses. Doctors working at hospitals and clinics can use the current information in their practices to develop better patient-specific regimens and treatments. Also, record files can be created to evidence progress in the field or for archival purposes.

Clearly, the genotype and phenotype information collected in base 108 as discussed above can pertain to pathogens or any other organic materials affecting a human phenotype. Also, other applications for knowledge base 108 will be apparent to a person skilled in the art.

MODIFICATIONS AND SCOPE

It is obvious that the gene sequencing apparatus described can be substituted by another gene analysis device. Many diseases can be identified by genetic characteristics other than that of a gene sequence. For example, karyotyping can easily identify cri-du-chat syndrome due to a deletion in chromosome 5, as well as Down's syndrome due to an extra chromosome 21. Such information can easily be entered into the health monitor and used in much the same way as a gene sequence.

From the above description, it is also apparent that the invention allows the consolidation of activities related to diagnosis and treatment of a genetic or pathogen-caused disease. Instead of sequencing a gene in a lab, having a technician interpret the results, looking up information about the disease in a reference, and then devising a treatment, a health care provider is able to do all four procedures in his or her office. The diagnosis and treatment of a patient becomes more efficient, and time and money are saved. In addition, due to the nature of the health monitor, the proposed system is small, portable, and easy to use.

Another benefit of the invention is that it creates a dynamic disease database that can be easily referenced. Although there are many references available for a health care provider to learn about the symptoms and characteristics of a disease, such information is static and must be updated constantly. This information is not consolidated, as well, often making providers look through many different resources. The system of invention allows information about a disease to be continually added to a single database. In addition, because each individual patient adds information about his or her disease state, the database provides quantitative as well as qualitative information. This allows health care providers to make statistical observations about disease incidence, frequency, or symptoms.

For example, 87% of the patients with phenylketonuria (PKU) who consume aspartame (i.e. NutraSweet) exhibit a more severe disease phenotype. A dynamic database built up by using the system of the invention is an invaluable resource not only for health care providers and patients, but epidemiologists, public health officials, and researchers. It has the potential to become an important tool for the health care field.

Another benefit of the proposed invention concerns genetic testing for prospective parents. Parents who suspect they are carrying a recessive disease allele can use the system to identify their chances of having an affected child. In this embodiment, both parents have their genome sequenced for the suspect disease allele for, as an example, Tay-Sachs disease. Their gene sequences are interpreted by the health monitor and sent via network to the database, which would carry known Tay-Sachs gene sequences. The parents' gene sequences are compared with the known Tay-Sachs gene sequences. The probability of their having an affected child is then calculated and sent back to the parents, with an accompanying script, if desired. If the parents have a high chance of conceiving an affected child, the script may suggest counseling or other awareness programs. An advantage of this embodiment is that it allows both parents to deal efficiently and in a private manner with this sensitive subject.

What is claimed is:

1. A system for developing a personalized treatment, the system comprising:
   a) a means for sequencing a gene and for providing at least one patient-specific gene sequence;
   b) a database of known gene sequences and associated scripts assigned to said known gene sequences; and
   c) a health monitor for interpreting said at least one patient-specific gene sequence, for receiving said associated scripts from said database, for presenting said associated scripts to a patient and for determining a degree of expressivity of a phenotype associated with a genotype based on a response of the patient to said associated scripts.

2. The system of claim 1, wherein said associated scripts comprise questions about the patient's environment and lifestyle.

3. The system of claim 2, wherein said health monitor presents said associated scripts to the patient more than once.

4. The system of claim 1, wherein said means for sequencing a gene allows analysis of said gene.

5. The system of claim 1, wherein said database is remote from said health monitor and connected to said health monitor by means of a network.

6. The system of claim 1, wherein said response of the patient to said associated scripts is used to construct a genotype-to-phenotype map.

7. The system of claim 1, wherein said response of the patient to said associated scripts is used to construct a genotype phenotype knowledge base.

8. The system of claim 1, wherein said at least one patient-specific gene sequence is associated with a disease condition.

\* \* \* \* \*